US012558083B2

(12) United States Patent
Collazo

(10) Patent No.: US 12,558,083 B2
(45) Date of Patent: Feb. 24, 2026

(54) PISTOL GRIP JOINT TENSIONER

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 559 days.

(21) Appl. No.: 17/965,423

(22) Filed: Oct. 13, 2022

(65) Prior Publication Data

US 2023/0121067 A1 Apr. 20, 2023

Related U.S. Application Data

(60) Provisional application No. 63/256,248, filed on Oct. 15, 2021.

(51) Int. Cl.
*A61B 17/02* (2006.01)
*A61B 17/34* (2006.01)
(52) U.S. Cl.
CPC ........ *A61B 17/025* (2013.01); *A61B 17/3417* (2013.01); *A61B 17/3468* (2013.01)
(58) Field of Classification Search
CPC .............. A61B 17/025; A61B 17/3417; A61B 17/3468
See application file for complete search history.

(56) References Cited

U.S. PATENT DOCUMENTS

| | | | |
|---|---|---|---|
| 5,116,338 | A | 5/1992 | Poggie et al. |
| 5,213,112 | A | 5/1993 | Niwa et al. |
| 7,641,664 | B2 | 1/2010 | Pagano |
| 7,651,500 | B2 | 1/2010 | Supper et al. |
| 7,828,727 | B2 | 11/2010 | Bhatnagar et al. |
| 8,034,088 | B2 | 10/2011 | Pagano |
| 8,337,508 | B2 | 12/2012 | Lavallee et al. |
| 8,430,885 | B2 * | 4/2013 | Manzi ................ A61B 17/8852 |
| | | | 606/86 A |
| 9,282,956 | B2 | 3/2016 | Fairneny |
| 9,498,199 | B2 * | 11/2016 | Colquhoun .......... A61B 17/025 |
| 2005/0182417 | A1 * | 8/2005 | Pagano .............. A61B 17/8811 |
| | | | 606/92 |
| 2005/0256527 | A1 | 11/2005 | Delfosse et al. |

(Continued)

FOREIGN PATENT DOCUMENTS

| | | |
|---|---|---|
| AU | 2019319868 A1 | 2/2021 |
| DE | 202004015215 U1 | 11/2004 |

(Continued)

*Primary Examiner* — Kevin T Truong
*Assistant Examiner* — Diana Jones
(74) *Attorney, Agent, or Firm* — Lerner David LLP

(57) ABSTRACT

Disclosed herein are a joint distractor for joint distraction and a method for utilizing the same in a joint distraction procedure. The joint distractor may include a first surface and a second surface. The first surface may contact a first bone of a joint and the second surface may contact a second bone of a joint. The first surface may be a flexible surface that is substantially parallel to the second surface in a first position and forms an arch in a second position to distract the first bone from the second bone. A method for distracting a joint may utilize the first and second surfaces of the joint distractor.

18 Claims, 13 Drawing Sheets

(56)         References Cited

U.S. PATENT DOCUMENTS

| | | | |
|---|---|---|---|
| 2007/0239157 A1* | 10/2007 | Guillaume | A61B 17/155 |
| | | | 606/60 |
| 2008/0269766 A1 | 10/2008 | Justis | |
| 2009/0276048 A1 | 11/2009 | Chirico et al. | |
| 2013/0079679 A1* | 3/2013 | Roche | A61B 5/4566 |
| | | | 600/594 |
| 2013/0267959 A1 | 10/2013 | Engh | |
| 2019/0046217 A1* | 2/2019 | Rasmussen | A61B 17/025 |

FOREIGN PATENT DOCUMENTS

| | | | |
|---|---|---|---|
| WO | 2000078225 A1 | 12/2000 | |
| WO | 2012020460 A1 | 2/2012 | |

* cited by examiner

PISTOL GRIP JOINT TENSIONER

CROSS-REFERENCE TO RELATED APPLICATIONS

This application claims the benefit of the filing date of U.S. Provisional Patent Application No. 63/256,248 filed Oct. 15, 2021, the disclosure of which is hereby incorporated herein by reference.

FIELD OF INVENTION

The present disclosure relates to an apparatus and a method for performing orthopedic procedures, and in particular to an apparatus and a method for performing joint distraction during orthopedic procedures.

BACKGROUND OF THE INVENTION

Orthopedic procedures for joint replacement generally include replacing a subject's joint with prosthetic joint components. Proper soft tissue tension, joint alignment and balance are necessary for smooth and well-aligned joint movement. For example, in a total knee arthroplasty ("TKA") procedure, a tensor is positioned in the intra-articular joint space between a tibia and a femur to distract the joint and eliminate laxity of the medial and lateral collateral ligaments prior to finalizing bone cuts.

A tensor generally includes tibial and femoral paddles for contacting bone within the intra-articular joint space and a distraction mechanism located outside of the joint as the joint gap is typically too narrow to accommodate the distraction mechanism and paddles. Because the paddles are loaded during distraction, they typically each have a thickness sufficient to prevent plastic deformation while under such loading conditions. However, these thicknesses are typically so thick that they make it difficult to position the tensor in tight joint spaces, especially during the initial insertion prior to distracting the knee joint.

Furthermore, load sensors which can be used with the tensors to provide real-time ligament tension during the TKA must be placed in contact with the paddles to ensure that the load sensor are directly in line with the load path. These sensors further increase the size of the tensor paddles and increase the difficulty of locating the paddles in a tight joint space.

Therefore, there exists a need for a tensor and a method for distracting joints utilizing the same that overcomes the deficiencies of the prior art.

BRIEF SUMMARY OF THE INVENTION

Disclosed herein are tensors for joint distraction and methods for joint distraction using the same.

In a first aspect of the present invention a joint distractor is provided. A joint distractor according to this aspect may include a first surface and a second surface. The first surface may contact a first bone of a joint. The second surface may contact a second bone of a joint. The first surface may be a flexible surface. The first surface may be substantially parallel to the second surface in a first position. The first surface may form an arch in a second position to distract the first bone from the second bone.

Continuing in accordance with this aspect, a height of the arch in the second position may define a joint distraction distance between the first bone and the second bone. The height may be at least 5 mm.

Continuing in accordance with this aspect, the joint distraction may include a rod. The rod may contact a proximal end of the first surface to move the first surface from the first position to the second position. The joint distractor may include a lever and a handle. The rod may be configured to move the first surface from the first position to the second position by moving the lever toward the handle. The handle and lever may be parallel to each other such that an operator may grip the handle and lever with one hand. The height of the arch may be controlled by a distance between the handle and the lever.

Continuing in accordance with this aspect, a combined thickness of the first surface and the second surface in the first position may be less than 4 mm.

Continuing in accordance with this aspect, the joint distractor may include a sensor disposed between the first and second surfaces. The sensor may be a load sensor, the load sensor contacting at least one of the first and second surfaces.

Continuing in accordance with this aspect, the first surface may be a spring. The spring may be a leaf spring disposed in a housing at a distal end of the joint distractor. The leaf spring may be in an unstressed condition in the first position and a stressed condition in the second position. The leaf spring may be compressed in the second position.

Continuing in accordance with this aspect, the joint distractor may include a joint displacement level indicator.

In another aspect of the present disclosure, a method of distracting a joint is provided. A method according to this aspect may include the steps of placing a distal end of a joint distractor in a first position into a joint, and distracting the joint my moving a first flexible surface from a first position to a second position. The first flexible surface of the joint distractor may contact a first bone of the joint and a second surface of the joint distractor may contact a second bone of the joint. The first surface may be parallel to the second surface in the first position. The first surface may form an arch to distract the first bone from the second bone in the second position.

Continuing in accordance with this aspect, the step of distracting the joint may include a step of moving a rod attached to the first surface to move the first surface from the first position to the second position. The step of moving the rod may include a step of moving a lever of the joint distractor toward a handle of the joint distractor.

Continuing in accordance with this aspect, a height of the arch may be related to a distance between the lever and the handle. The height may be related to a distraction distance of the first bone from the second bone.

BRIEF DESCRIPTION OF THE DRAWINGS

A more complete appreciation of the subject matter of the present invention and the various advantages thereof can be realized by reference to the following detailed description, in which reference is made to the following accompanying drawings.

DETAILED DESCRIPTION

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described.

As used herein, the terms "tensor," "joint distractor," and "balancer" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the invention. As used herein, when referring to bones or other parts of the body, the term "anterior" means toward the front part or the face, and the term "posterior" means toward the back of the body. The term "medial" means toward the midline of the body, and the term "lateral" means away from the midline of the body. The term "superior" means closer to the heart, and the term "inferior" means more distant from the heart.

Figure 1:
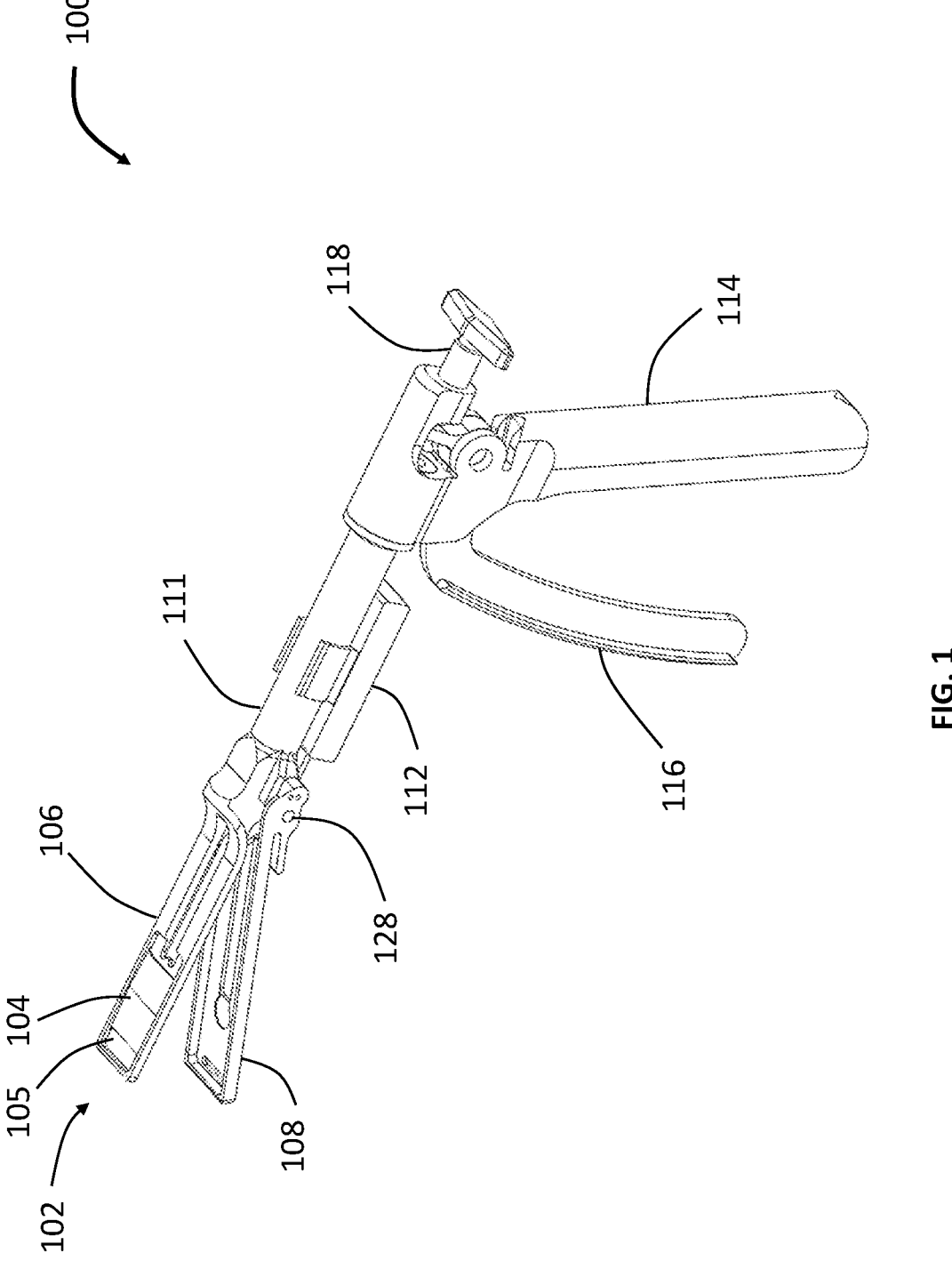
FIG. 1 is a perspective view of a tensor according to an embodiment of the present disclosure.

FIG. 1 shows a perspective view of a tensor 100 according to an embodiment of the present disclosure. Tensor 100 includes a distal end 102 with an upper housing 106 and a lower housing 108. Upper housing 106 and lower housing 108 are connected at a hinge 128 which allows the upper and lower housing 106, 108 to pivot about this hinge as shown in FIG. 1. Upper housing 106 includes a leaf spring 104 disposed within a recess 105 therein such that at least one end of leaf spring 104 is secured to or abuts upper housing 106 for joint distraction as more fully explained below. A housing 111 contains a rod or plunger 110 connected to another end of the leaf spring 104 allows a user to compress leaf spring 104 for joint distraction. An opposite end of the plunger engages a lever or cam 119 at an end of an actuating lever 116. Plunger 110 is disposed within plunger housing 111 and is slidable therein. Plunger housing is integral with upper housing 106 and a handle 114 so as to form a monolithic structure. Actuating lever 116 is pivotable relative to handle 114 and forms a pistol grip like mechanism that offers a convenient means for an operator to grip and actuate tensor 100 with one hand.

Tensor 100 described herein is configured to be placed in a subject's knee joint in an anterior-to-posterior direction, posterior-to-anterior, medial-to-lateral, or lateral-to-medial direction. While a total knee arthroplasty ("TKA") procedure is generally described in these embodiments, the apparatus and methods of the present disclosure can be used for various other knee and hip procedures, such as a partial knee arthroplasty, or any part of these procedures.

Figure 2:
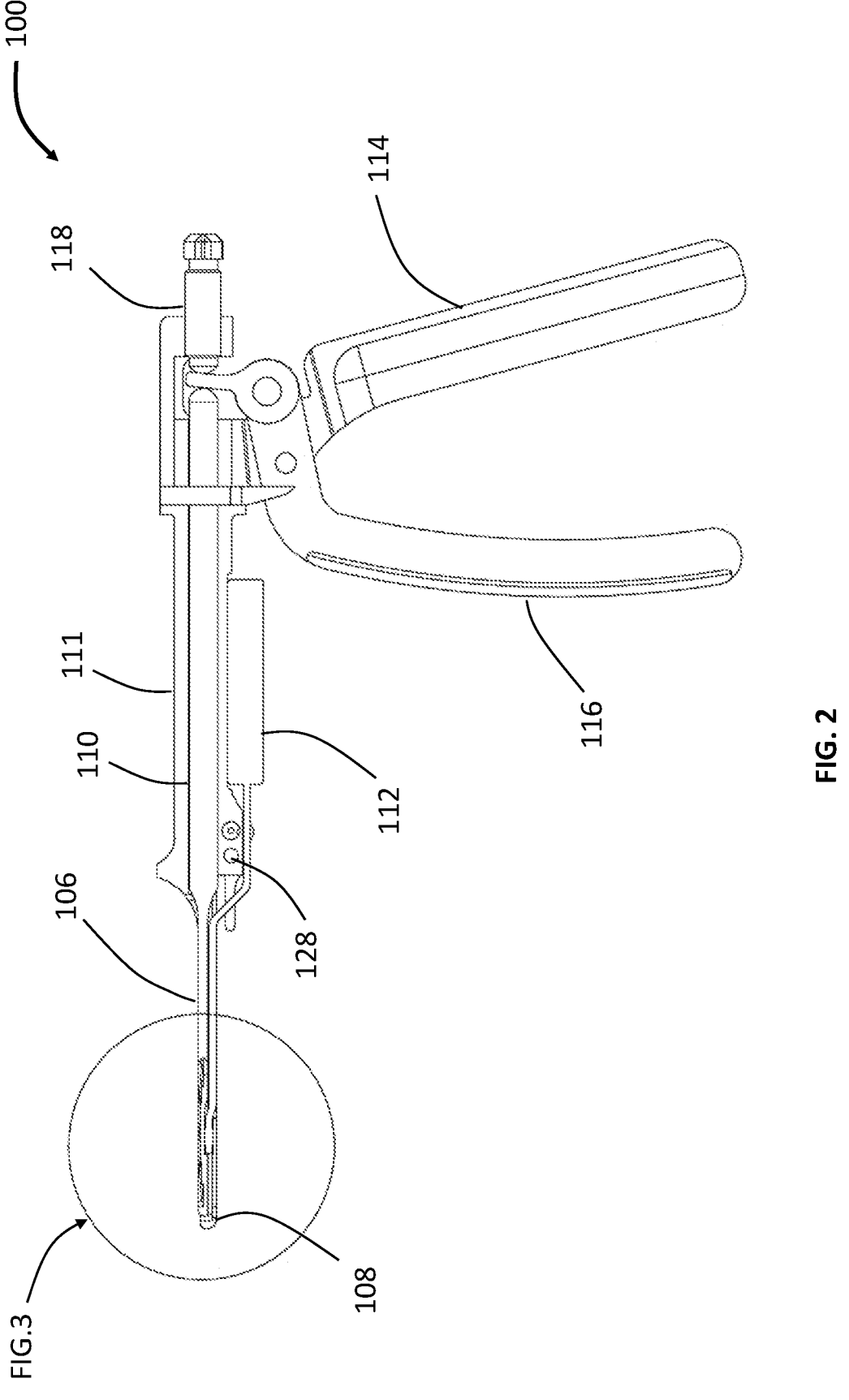
FIG. 2 is a side view of the tensor of FIG. 1 in a first position.
Figure 3:
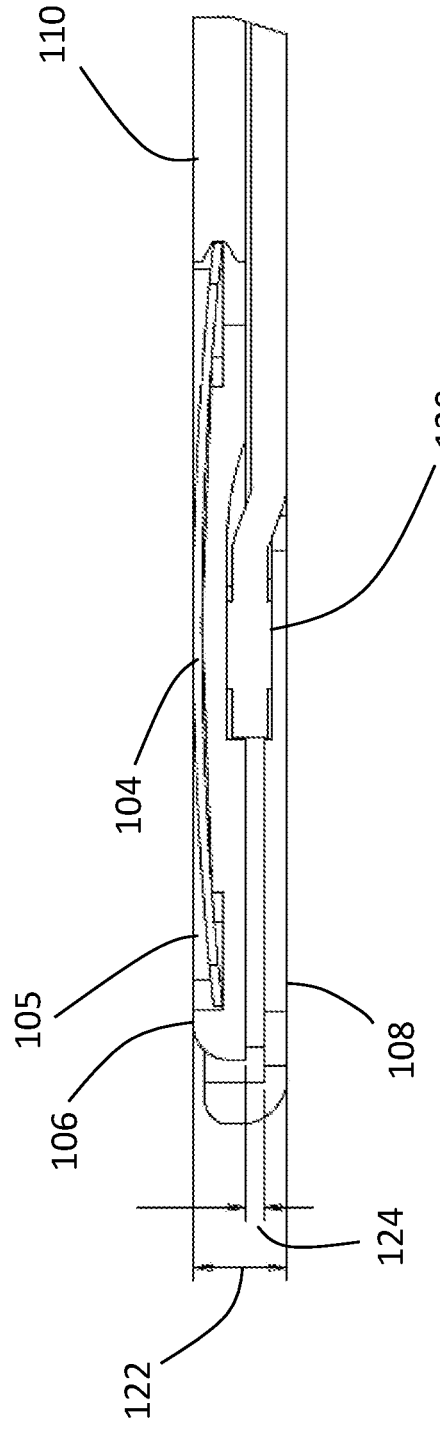
FIG. 3 is a partial side view of a distal end of the tensor of FIG. 2.
Figure 5:
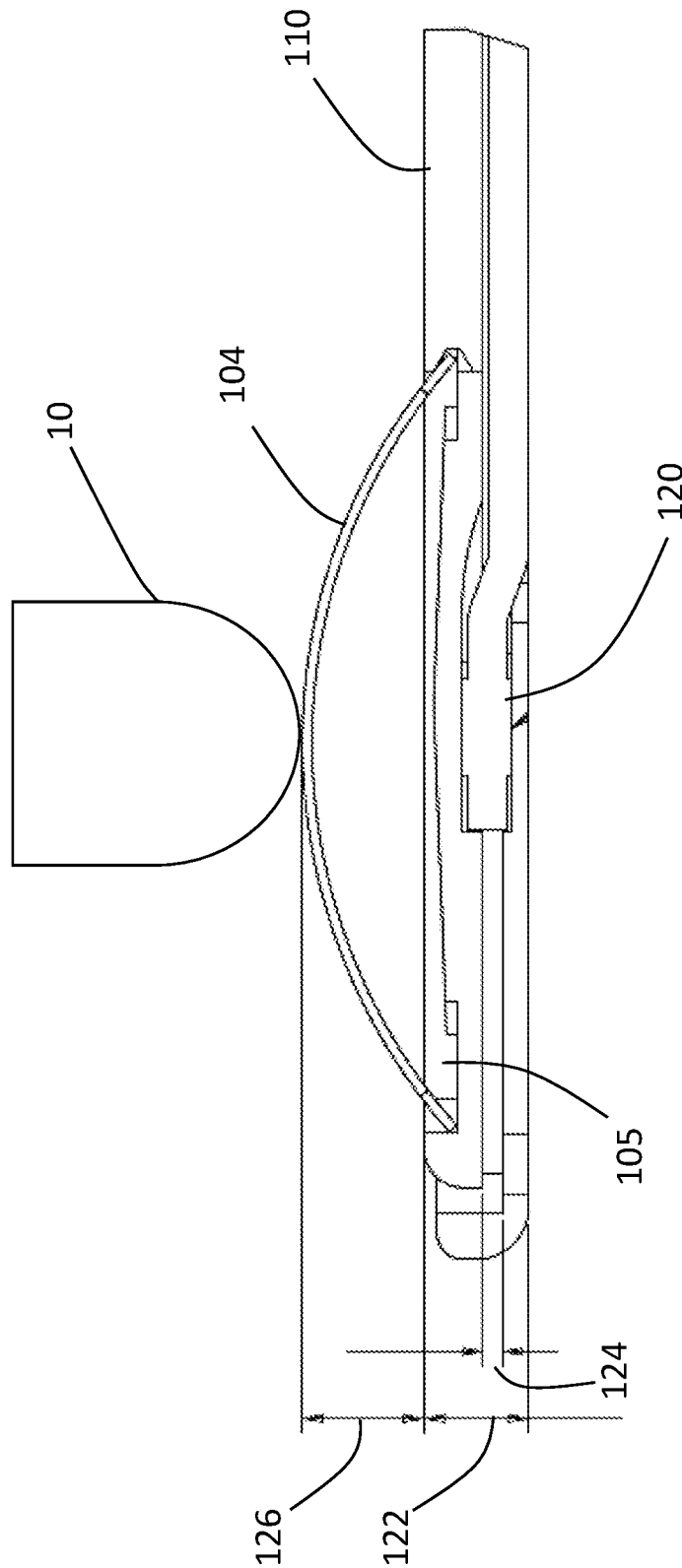
FIG. 5 is a partial side view of the distal end of the tensor of FIG. 4.

Referring now to FIGS. 2 and 3, tensor 100 is shown in a first position where leaf spring 104 is in a retracted unstressed state. Leaf spring 104 lies flat within upper housing 106 in the unstressed state when no forces are acting on the leaf spring—i.e., when actuating lever 116 is not engaged. This allows distal end 102 of tensor 100 to have a thin low profile for easy insertion into tight and narrow joint spaces. For example, distal end 102 can have a thickness 122 of 4 mm or less in one embodiment. A load cell 120 is located directly below leaf spring 104 in a gap 124 between upper housing 106 and lower housing 108 as best shown in FIG. 3. Gap 124 in one embodiment can be 0.75 mm to accommodate a load cell. A load sensor housing 112 including load cell circuitry and processor for calculating and transmitting intra-articular load data to an eternal source are connected directly adjacent the upper and lower housing and below plunger 110 as shown in FIG. 2. In another embodiment, tensor 100 can include a display located on the tensor to indicate the load value measure by load cell 120. The location of load cell 120 below leaf spring 104 ensures that the load from a femur and tibia is transferred directly to load cell 120. In this regard, load is transferred from leaf spring 104 to upper housing 106 and consequently to load cell 120. As shown in FIG. 5, load cell 120 is positioned below and between the two ends of leaf spring 104 to ensure load cell 120 realizes the entire load applied to leaf spring 104. The direct contact of load cell 120 to the joint bones significantly improves the load reading as the load cell is not shielded or buttressed through any adjoining structures which can prevent accurate load measurement. The load sensor housing can be removably attached to housing 111. Upper housing 106 and lower housing 108 can be separated by pivoting these structures at hinge 128 to conveniently access and replace load cell 120. Load cell 120 can be a strain gauge load cell (e.g., single point load cell, planar beam load cell, bending beam load cell, shear beam load cell, etc.), pneumatic load cell, hydraulic load cell, piezoelectric load cell or any other load cell type.

Figure 4:
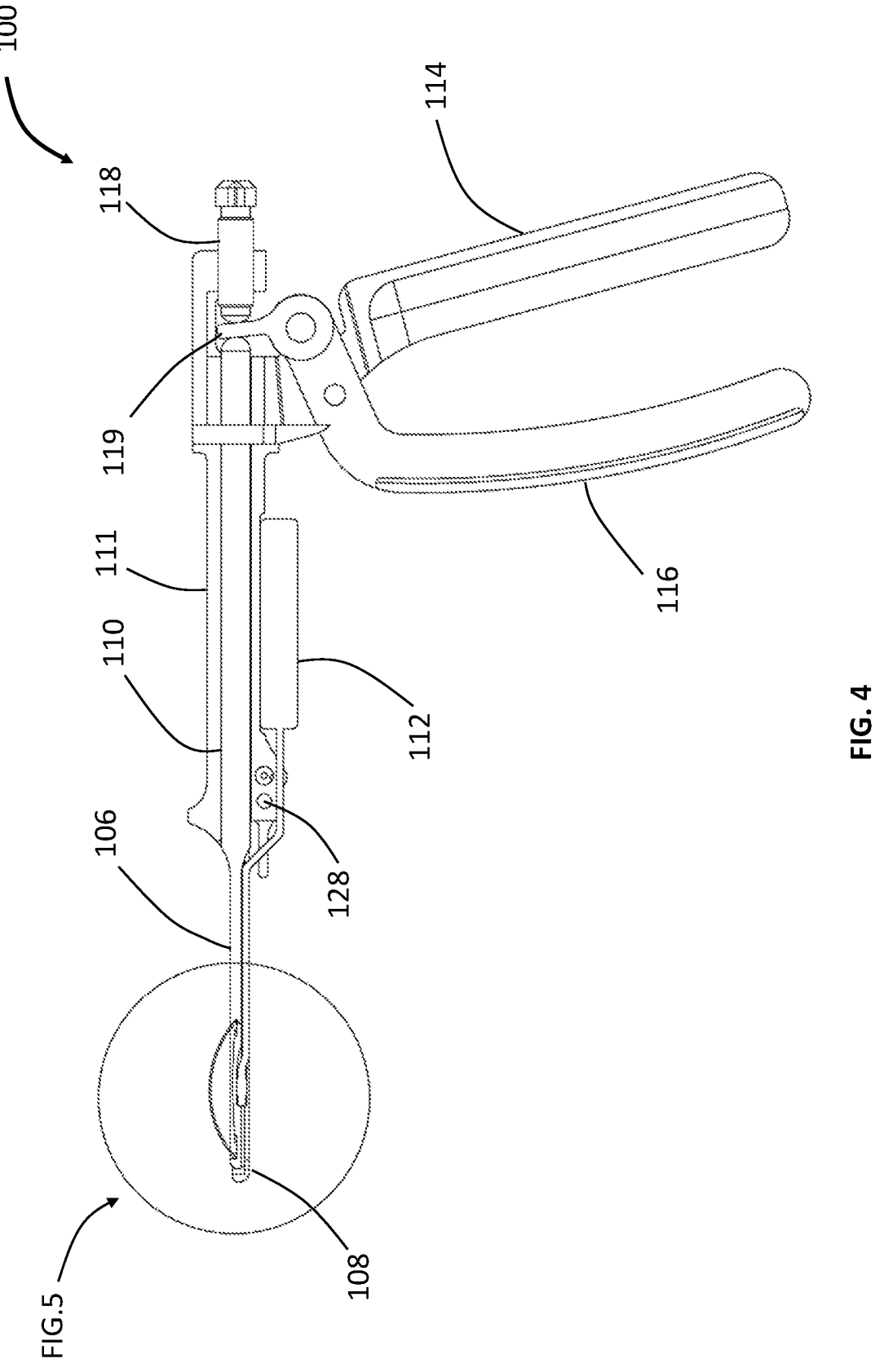
FIG. 4 is a side view of the tensor of FIG. 1 in a second position.

FIGS. 4 and 5 show tensor 100 in a second position where leaf spring 104 is in a compressed state. This compressed state is achieved by pushing actuating lever 116 toward handle 114. In the compressed state, leaf spring 104 is axially compressed to form an arch of variable height. The height of this arch can be adjusted by varying the distance between the actuating lever 116 and handle 114. A locking screw 118 is used to fix leaf spring at a specific height and prevent the compressed leaf spring from returning to its unstressed state. In this regard, locking screw 118 abuts cam 119 preventing its rotation away from plunger 110 so that plunger 110 maintains its compressive force on leaf spring 104. An operator can squeeze actuating lever 116 toward handle 114 until a required joint distraction is achieved, and then lock tensor 100 by advancing locking screw 118 unit it contacts cam 119 to maintain the arch height as best shown in FIGS. 4 and 5. For example, an arch height 126 of 5 mm is shown in FIG. 5. While the arch shown in FIG. 5 is a rounded arch, any parabolic shape or other shapes can be formed by leaf spring 104 in a compressed state depending on the size, material, and load on the leaf spring.

As shown in FIG. 5, leaf spring 104 is an intra-articular distraction mechanism which distracts a knee joint by directly contacting and pushing a femur 10 when compressed. The thin low profile of distal end 102 allows an operator to place tensor 100 directly into the joint and distract the knee joint. Using the arch of leaf spring 104 to distract the joint utilizes the inherent structural ability of an arch to carry significant amounts of compressive loads relative to its size. Tensors using paddles or other prying members experience bending moments since the applied load is external to the joint space and at a distance away from the reactive load which is within the joint space and are therefore designed with ample cross-sectional thickness to withstand the applied loads without plastic deformation. Conversely, the arch of leaf spring 104 is capable of withstanding large loads relative to its size because the load is distributed along its curvature and is therefore not a bending load, but rather a compressive load. Many materials, such as stainless steel, are generally stronger in compression than in tension. Thus, leaf spring 104 allows tensor 100 to have low thin profiled distal end 102 to facilitate insertion into tight joint spaces without comprising on tensor distraction force. Upon releasing the force on actuating lever 116, or releasing locking screw 118—the inherent spring force of leaf spring 104 in combination with compressive load of the distracted joint space will cause plunger 110 to retract and the spring to reverse course going from a stressed (arch) to an unstressed (flat) condition.

Figure 6:
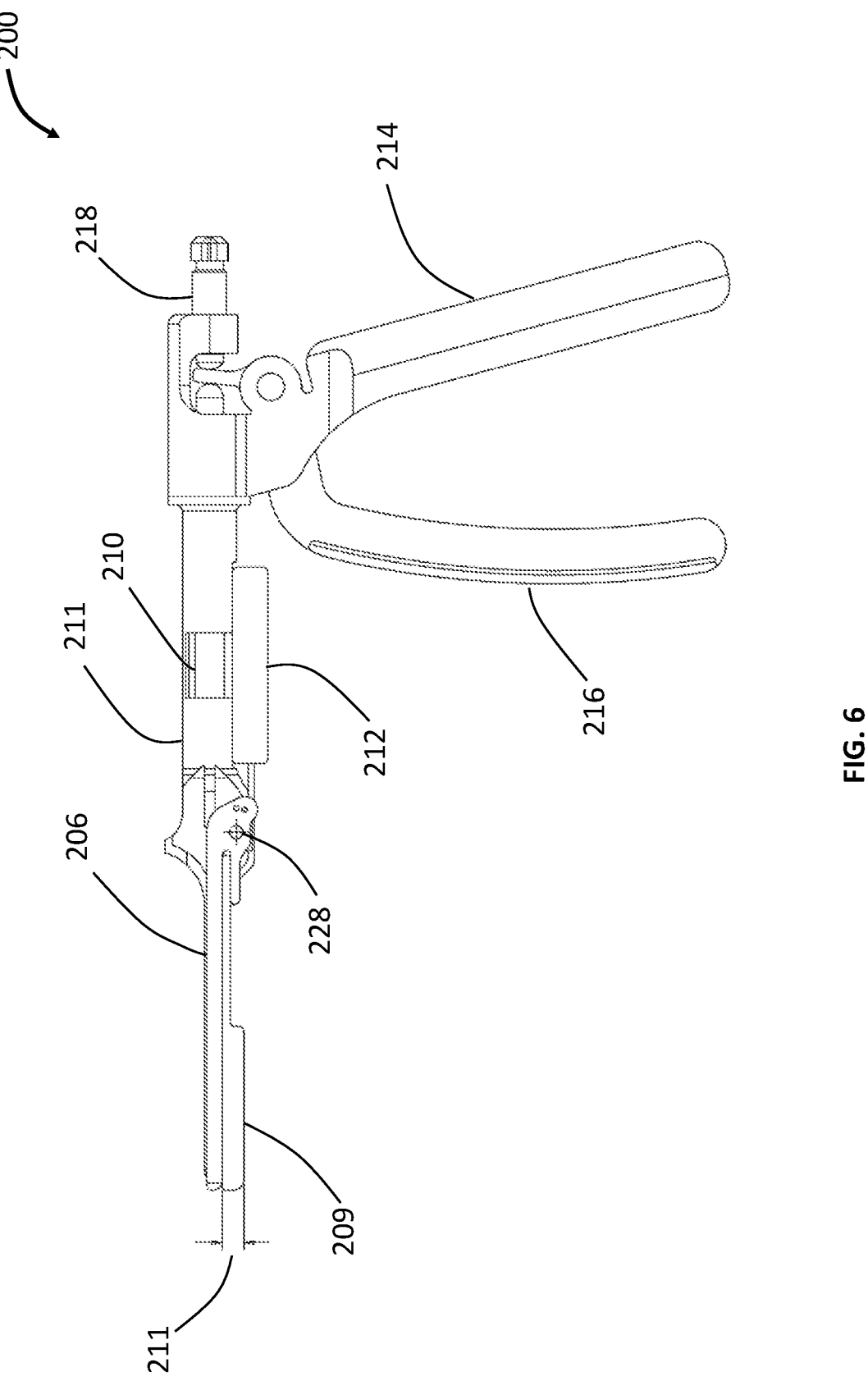
FIG. 6 is a side view of a tensor according to another embodiment of the present disclosure.

FIG. 6 shows a side view of tensor 200 according to another embodiment of the present disclosure. Tensor 200 is similar to tensor 100, and therefore like elements are referred to with similar numerals within the 200-series of numbers. For example, tensor 200 includes an upper housing 206 connected to a plunger housing 211, a handle 214 and an actuating lever 216. Also, a plunger 210 is disposed within plunger housing 211, and actuating lever 216 is moveable relative to handle 214. However, unlike tensor 100, tensor 200 includes a spacer block 209 attached to lower housing 208. Spacer block 209 can be removably attached to lower housing 208 by pivoting upper and lower housing at hinge 228. Spacer block 209 allows tensor 200 to be used for joint spaces that exceed the maximum distraction capacity of the tensor. For example, such as in revision surgery, a spacer block can be removably attached to the distal housing to increase the overall distraction by a distance 211 as shown in FIG. 6. In one embodiment, multiple spacers of varying height can be provided in a kit to allow an operator to select a specific spacer based on the required joint distraction.

Figure 7:
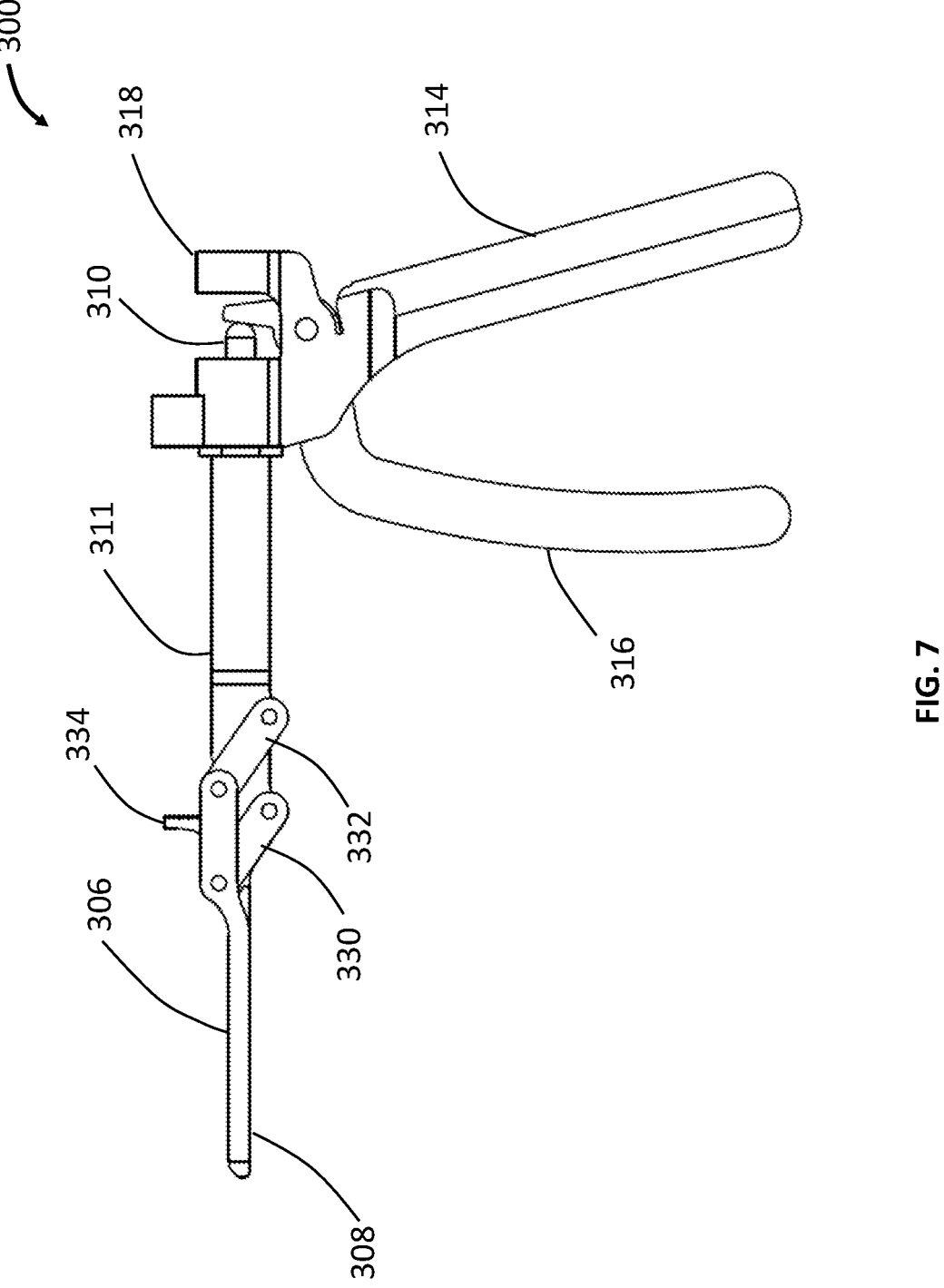
FIG. 7 is a side view of a tensor in a first position according to another embodiment of the present disclosure.

Referring now to FIG. 7, there is shown a tensor 300 according to another embodiment of the present disclosure. Tensor 300 is similar to tensor 100, and therefore like elements are referred to with similar numerals within the 300-series of numbers. For example, tensor 300 includes an upper housing 306, lower housing 308, plunger housing 311, plunger 310 slidably disposed within plunger housing 311, a handle 314 and an actuating lever 316. However, unlike tensor 100, tensor 300 does not include a load sensor but has a 4-bar linkage system to tactically assess ligament tension via a proprioceptive/tactile feedback on the operator's hand through the resistance on actuating lever 316 and handle 314. In this regard, lower housing 308 is integrally connected to plunger housing 311 while upper housing 306 is moveably connected to plunger housing via linkages 330 and 332 of the 4-bar linkage. Also, upper housing 306 includes a femur contacting load plate 336 (see FIG. 8), and a leaf spring 304 is mounted within lower housing 308 directly beneath load plate 336. Bars 330 and bars 332 form a constant parallelogram to ensure that femur contacting load plate 336 is always horizontal and in tangential contact with leaf spring 304.

Figure 8:
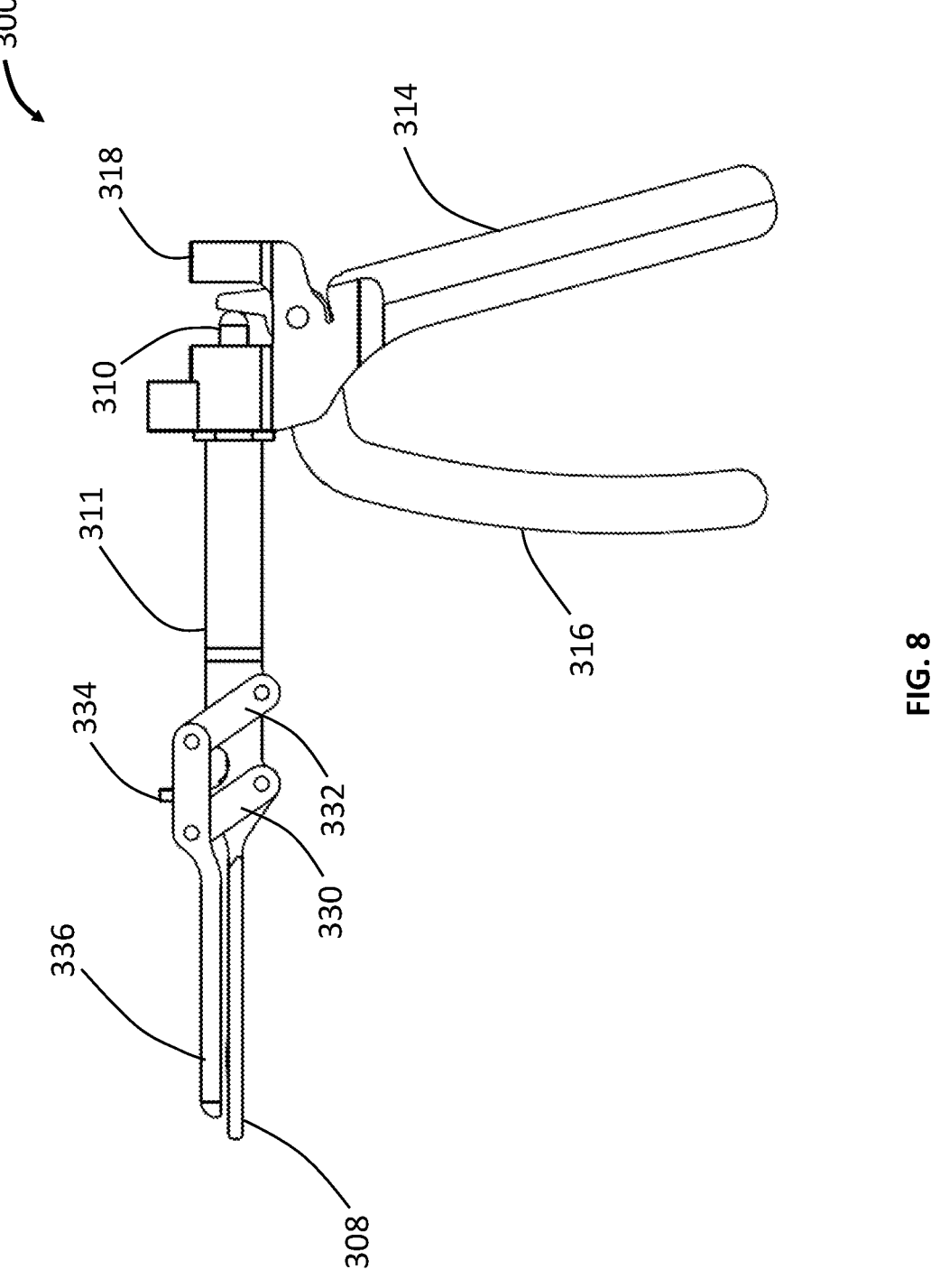
FIG. 8 is a side view of the tensor of FIG. 7 in a second position.
Figure 9:
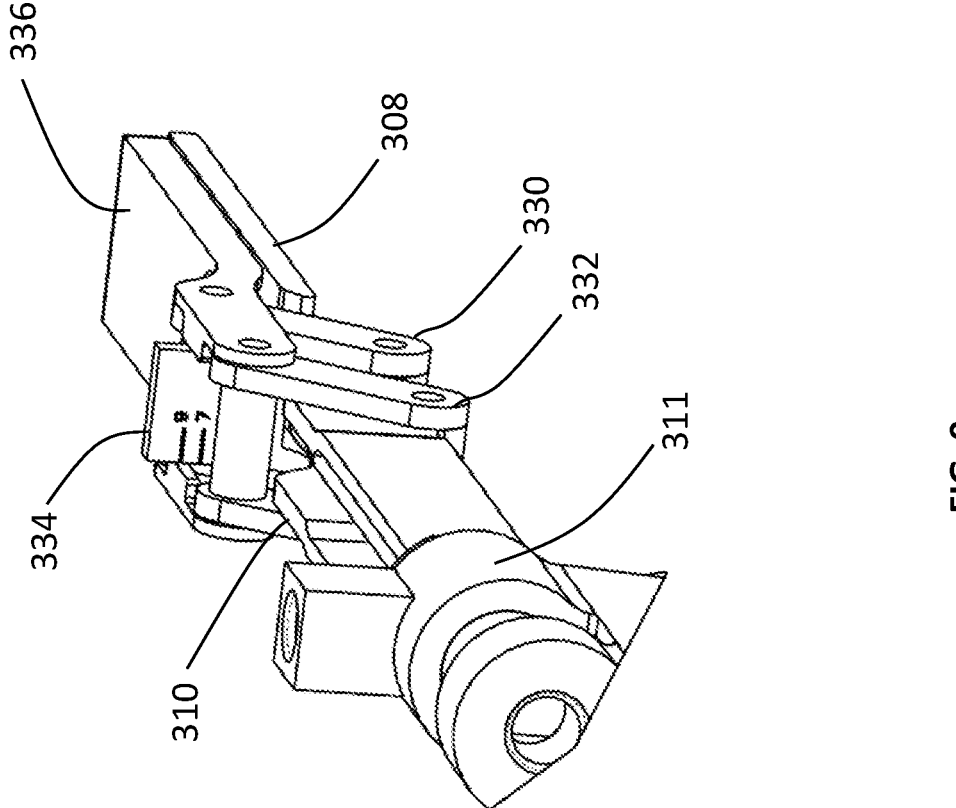
FIG. 9 is a partial back perspective view of the tensor of FIG. 8.

FIG. 8 shows leaf spring 304 of tensor 300 in a compressed state. Femur contacting load plate 336 is forced away from lower housing when an operator engages actuating handle 316. A displacement indicator 334, which is a cross-bar connected to opposed linkages 332 of the 4-bar linkage, located on tensor 300 shows the distraction height as best shown in FIG. 9. Thus, as upper housing 306 rises and falls, displacement indicator 334 simultaneously rises and falls to indicate the nominal displacement.

Figure 10:
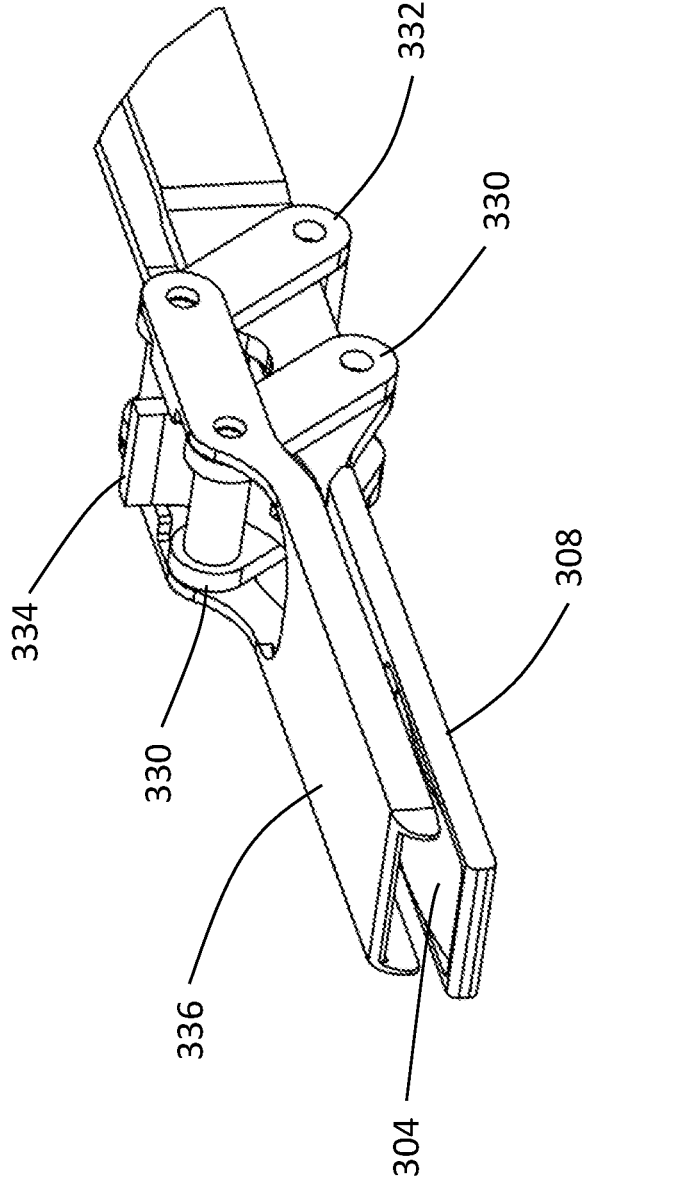
FIG. 10 is a partial front perspective view of the tensor of FIG. 8.

FIG. 10 show a close-up view of the distal end of tensor 300 with the leaf spring in a compressed state. As seen here, bars 330 and bars 332 form a parallelogram to ensure that femur contacting load plate 336 is in tangential contact with leaf spring 304. This ensures that a femoral load is always transferred through the apex of leaf spring 304 for a symmetrical load distribution on leaf spring. The 4-bar linkage parallelogram ensures that amount of distraction occurring within the joint space is identical to the amount indicated on the readout display outside the joint space. While joint distraction height is shown in displacement indicator 334 in tensor 300, joint distraction height can be electronically communicated to an external source in other embodiments. Tensor 300 can also be included with a load sensor similar to the load sensor configuration described above in tensors 100, 200.

Figure 11:
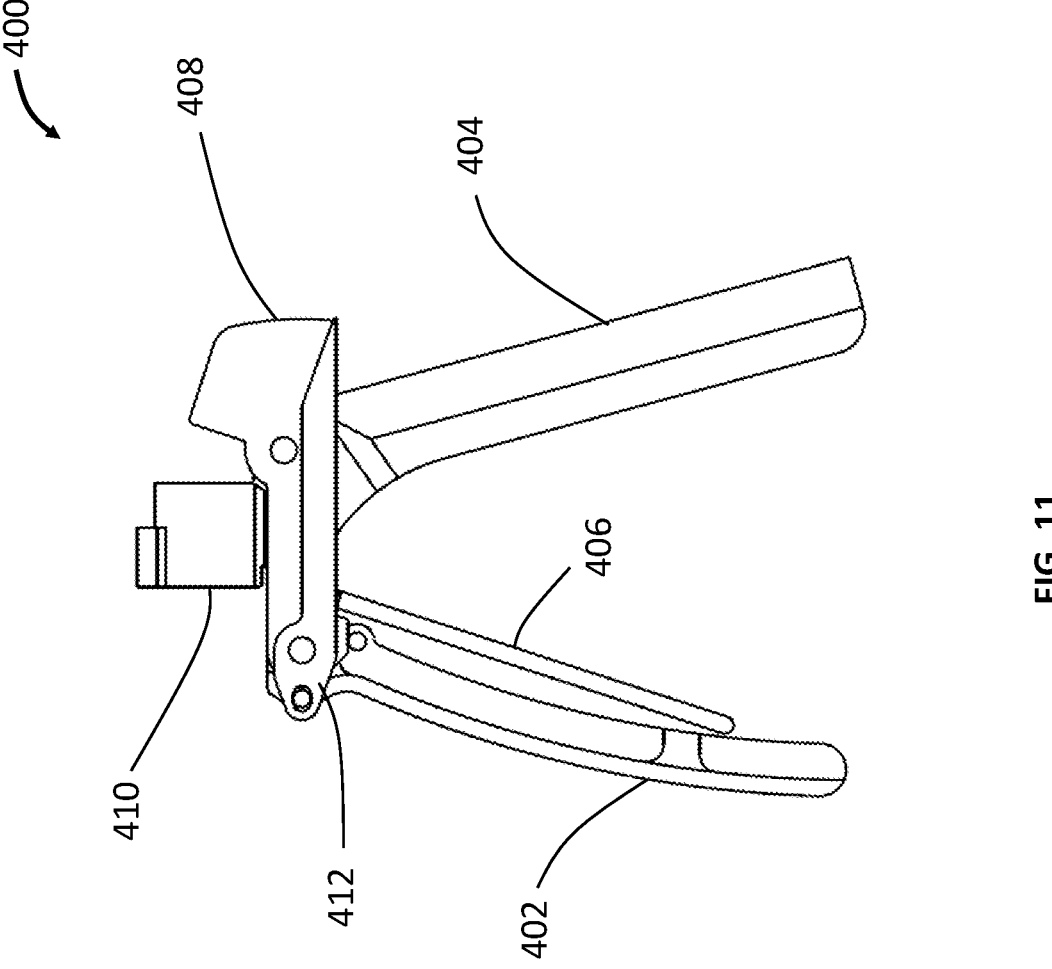
FIG. 11 is a side view of a handle assembly in a first position according to an embodiment of the present disclosure.
Figure 12:
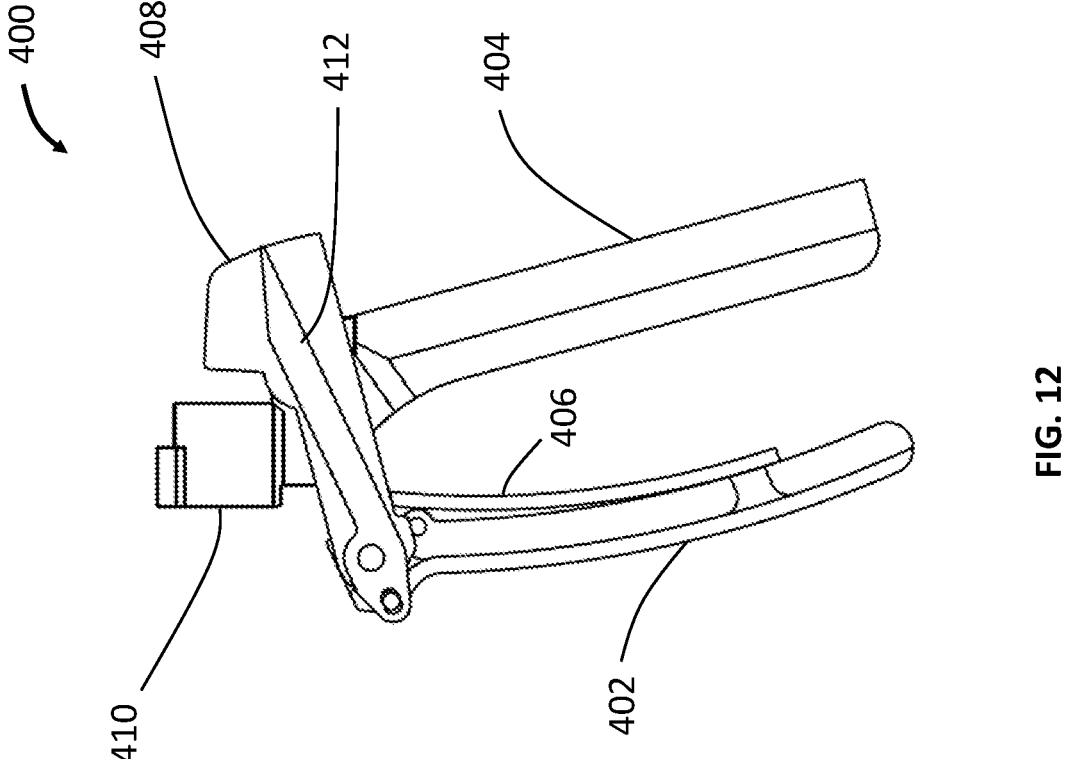
FIG. 12 is a side view of the handle assembly of FIG. 11 in a second position.
Figure 14:
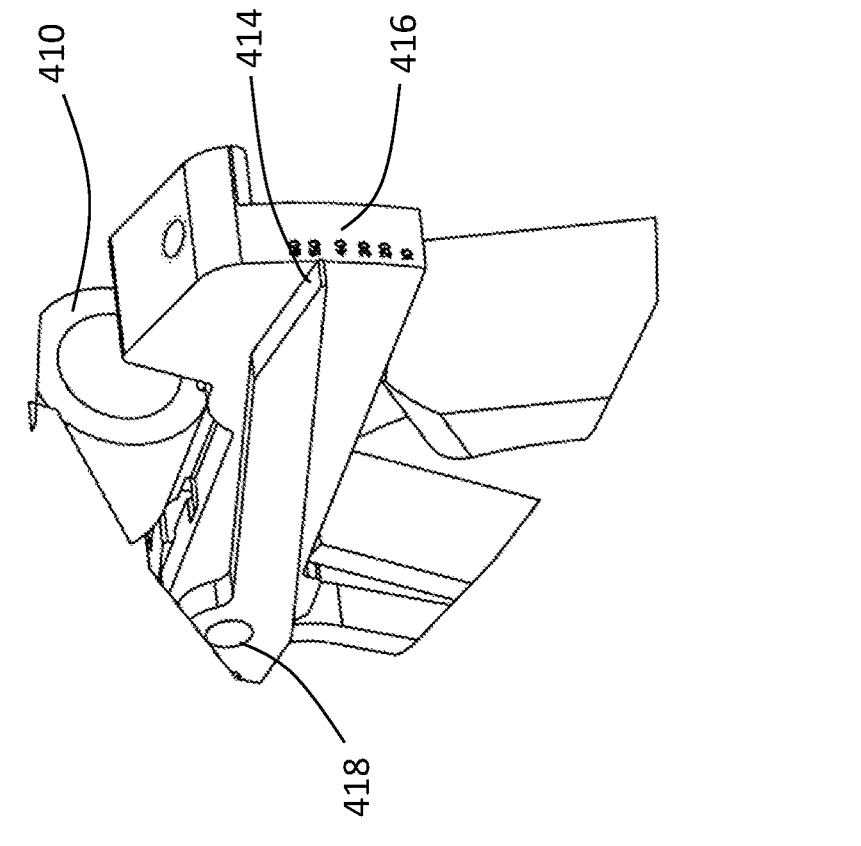
FIG. 14 is a partial front view of the handle assembly of FIG. 13.
Figure 13:
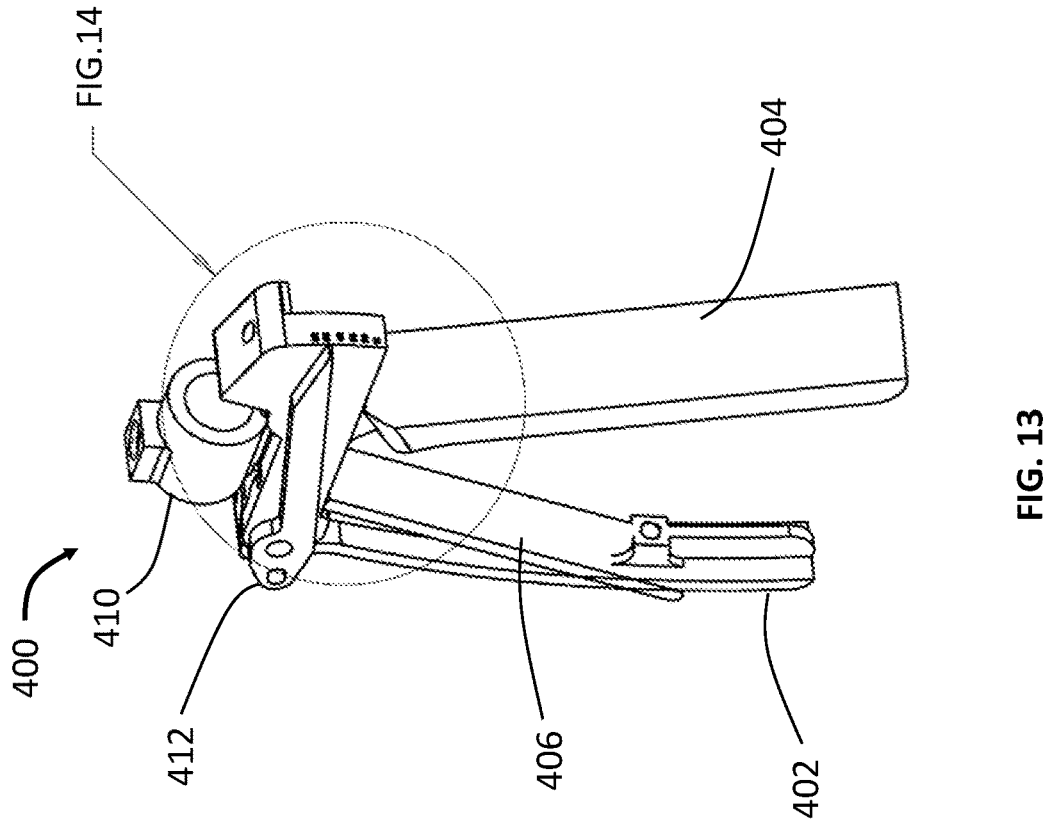
FIG. 13 is an isometric front view of the handle assembly of FIG. 12.

FIGS. 11-14 show a handle assembly 400 according to another embodiment of the present disclosure. Handle assembly 400 includes an actuating lever 402 and a handle 404 opposite the actuating lever. Handle assembly 400 can be attached to a tensor via a mount 410 on a housing 408 of the handle assembly. Mount 410 can be integral to handle 404. Instead of a load sensor described in tensors 100, 200, a mechanical deflection member such as a leaf spring 406 is used in this embodiment to measure distraction force. Leaf spring 406 is connected to actuating lever 402 as shown in FIG. 11 and functions as a deflection member to measure distraction force. FIG. 11 shows leaf spring 406 in an unstressed neutral state when the handle assembly and attached tensor are in a neutral unstressed condition. When an operator squeezes actuating lever 402 toward handle 404 to perform a distraction, leaf spring 406 deflects as shown in FIG. 12. Any force applied to actuating lever 402 to distract the tibial and femoral paddles or plates of the tensor is transmitted through leaf spring 406 causing a deflection of the leaf spring. A force indicator 412 element connected to the leaf spring is positioned to translate about a pivot 418 in response to the leaf spring deflection. A pointer 414 of the force indicator 412 indicates the distraction force via gradations 416 as shown in FIGS. 13 and 14. Spring deflection, as indicated by the displacement of indicator 412, is calibrated to represent the distraction force. Leaf spring 406 stiffness and/or force indicator translation can be calibrated to account for the initial force required to compress intra-articular distraction element such as leaf spring 104 of tensor 100. For example, stiffness of leaf spring 406 can be selected to provide only a small deflection when subjected to the initial force required to fully compress the intra-articular distraction element, and provide greater sensitivity—i.e., deflection, when subjected to forces greater than this initial force. Alternatively, the indicator translation can be adjusted to read out the force required to fully compress the intra-articular distraction element, and display only the joint distraction force. Thus, tensors disclosed herein can be used with load sensors or mechanical deflection members such as leaf springs, or any combination thereof, to measure distraction force.

While tensors with leaf springs are described above, other embodiments can have tensors with helical compression springs, torsion springs, disc springs, conical springs, etc. as intra-articular distraction members. In another embodiment, a tensor can be provided with a kit including multiple leaf springs of varying compression strengths to allow an operator to select and place a particular leaf spring in the upper or lower housing based on the distraction required for a particular procedure. While a load senor and load cell are described above, other embodiments of the tensor can have other sensors such as accelerometers, gyroscopes, magnetometers, inertial measuring units, thermometers, etc. Multiple sensors can be combined in a single tensor in other embodiments.

The inherent strength of a compact, thin-walled arch of the leaf spring and simplicity of the distraction mechanisms described herein allow for a compact, light tensor that can weigh less than 227 grams but at that can provide significant distraction force. The compact size of this tensor is ideal for unicompartmental knee replacement, bi-compartmental, uni knee replacement, ACL sparing knee replacement, etc. which require insertion of a tensor into tight joint spaces.

A method of distracting a joint using a tensor disclosed above is described according to an embodiment of the present disclosure. An operator can conveniently grasp tensor 100 in one hand by holding lever 116 and handle 114 to place tensor 100 into a joint. In an unstressed condition, the low thin profile of distal end 102 of tensor 100 allows easy insertion into tight joint spaces such that upper housing 106 contacts a femur and lower housing 108 contacts a tibia. The operator can then push lever 116 toward handle 114 to compress leaf spring 104. Compressing leaf spring 104 will cause the flat unstressed leaf spring 104 to form an arch. The height of the arch can be controlled by controlling the distance between lever 116 and handle 114. When the required distraction gap is achieved, leaf spring 104 compression can be locked in place using locking screw 118 to prevent the leaf spring from returning to an unstressed condition. Upon completion of the procedure, an operator can release locking screw 118 which will cause leaf spring 104 to return to an unstressed condition allowing distal end 102 of tensor to revert to the thin low profile. An operator can now conveniently remove tensor 100 from the joint space.

While the method above is described with reference to tensor 100, tensors 200 and 300 can be used instead of tensor 100 in other embodiments. While the method above is manually performed, other embodiments can use tensors of the present disclosure in robotic procedures.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the paragraphs below.

The invention claimed is:

1. A joint distractor comprising:
    an upper housing and a lower housing connected at a hinge;
    a first surface configured to contact a first bone of a joint, the first surface being a flexible surface of the upper housing, and;
    a second surface configured to contact a second bone of the joint, the second surface being defined by the lower housing;
    wherein the first surface is substantially parallel to the second surface in a first position, and forming an arch in a second position configured to distract the first bone from the second bone.

2. The joint distractor of claim 1, wherein a height of the arch in the second position is configured to defines a joint distraction distance between the first bone and the second bone.

3. The joint distractor of claim 2, wherein the height is at least 5 mm.

4. The joint distractor of claim 2, further including a rod, wherein the rod contacts a proximal end of the first surface to move the first surface from the first position to the second position.

5. The joint distractor of claim 4, further including a lever and a handle, wherein the rod is configured to move the first surface from the first position to the second position by moving the lever toward the handle.

6. The joint distractor of claim 5, wherein the handle and lever are parallel to each other such that an operator can grip the handle and lever with one hand.

7. The joint distractor of claim 6, wherein the height of the arch is controlled by a distance between the handle and the lever.

8. The joint distractor of claim 1, wherein a combined thickness of the first surface and the second surface in the first position is less than 4 mm.

9. The joint distractor of claim 1, further including a sensor disposed between the first and second surfaces.

10. The joint distractor of claim 9, wherein the sensor is a load sensor, the load sensor contacting at least one of the first and second surfaces.

11. The joint distractor of claim 1, wherein the first surface is a surface of a spring.

12. The joint distractor of claim 11, wherein the spring is a leaf spring disposed in a housing at a distal end of the joint distractor.

13. The joint distractor of claim 12, wherein the leaf spring is in an unstressed condition in the first position and a stressed condition in the second position.

14. The joint distractor of claim 12, wherein the leaf spring is compressed in the second position.

15. The joint distractor of claim 1, further including a joint displacement level indicator.

16. A joint distractor comprising: an upper housing and a lower housing; a first surface configured to contact a first bone of a joint, the first surface being a flexible surface of the upper housing, and a second surface configured to contact a second bone of the joint, wherein the first surface is substantially parallel to the second surface in a first position, and forming an arch in a second position configured to distract the first bone from the second bone, the joint distractor including a locking screw configured to secure the first surface in the second position; and wherein the upper housing is connected to the lower housing by a hinge.

17. The joint distractor of claim 16, further including a load sensor disposed in a gap between the upper housing and the lower housing.

18. A joint distractor comprising: a first surface configured to contact a first bone of a joint, the first surface being a flexible surface, and a second surface defining a flat surface configure to contact a second bone of the joint; wherein the first surface is substantially parallel to the second surface in a first position, and forming an arch in a second position configured to distract the first bone from the second bone, the first surface being resiliently biased to return from the arch in the second position to the first position upon release of a distraction force; and wherein the flexible surface is a leaf spring.

* * * * *